United States Patent [19]

Spacek et al.

[11] Patent Number: 4,968,421
[45] Date of Patent: Nov. 6, 1990

[54] COLUMN FOR LIQUID CHROMATOGRAPHY

[75] Inventors: Pavel Spacek; Stanislav Vozka; Jiri Coupek; Miroslav Kubin; Jaroslav Voslar; Bedrich Porsch, all of Prague, Czechoslovakia

[73] Assignee: Ceskoslovenska akademie ved, Praha, Czechoslovakia

[21] Appl. No.: 408,413

[22] Filed: Sep. 14, 1989

Related U.S. Application Data

[63] Continuation of Ser. No. 171,600, Mar. 22, 1988, abandoned, which is a continuation of Ser. No. 389,089, Jun. 16, 1982, abandoned.

[30] Foreign Application Priority Data

Jun. 19, 1981 [CS] Czechoslovakia .................. 4635-81
Jul. 23, 1981 [CS] Czechoslovakia .................. 56050-81

[51] Int. Cl.⁵ ............................................. B01D 15/08
[52] U.S. Cl. .................................. 210/198.2; 210/656; 55/386
[58] Field of Search ............... 210/656, 198.2; 55/386; 422/70

[56] References Cited

U.S. PATENT DOCUMENTS

| | | | |
|---|---|---|---|
| 3,440,864 | 4/1969 | Blume | 210/656 |
| 3,855,130 | 12/1974 | Randau | 210/198.2 |
| 3,878,099 | 4/1975 | Ogle | 210/198.2 |
| 4,026,803 | 5/1977 | Abrahams | 210/198.2 |
| 4,162,977 | 7/1979 | Guillemin | 210/198.2 |
| 4,280,905 | 7/1981 | Gunkel | 210/198.2 |
| 4,283,280 | 8/1981 | Brownlee | 210/198.2 |

FOREIGN PATENT DOCUMENTS

| | | | |
|---|---|---|---|
| 1193975 | 9/1985 | Canada | 210/198.2 |
| 68343 | 10/1986 | European Pat. Off. | 210/198.2 |

OTHER PUBLICATIONS

Kirk-Othmer-Encyclopedia of Chemical Technology, 3rd Edition, New York, John Wiley & Sons, vol. 22, 1980, p. 870.

Primary Examiner—Ernest G. Therkorn
Attorney, Agent, or Firm—Klein & Vibber

[57] ABSTRACT

Column for liquid chromatography contains a glass tube for sorbent packing closed with simple column seals and inserted into a jacket made of metal or plastic material. The jacket transfers axial forces exerted on the column seals by liquid pressure action by means of sockets. It secures the tightness of the column, enables the connection of the column to a chromatographic system, and has a protective function at the same time. The columns can be coupled in series by means of doubled sockets.

9 Claims, 3 Drawing Sheets

COLUMN FOR LIQUID CHROMATOGRAPHY

This application is a continuation of application, Ser. No. 171,600, filed Mar. 22, 1988, which in turn is a continuation of Ser. No. 389,089, filed June. 16, 1982, both now abandoned.

FIELD OF THE INVENTION

This invention pertains to a column for liquid chromatography.

BACKGROUND OF THE INVENTION

To achieve a high efficiency of separation in liquid chromatography, metallic columns (tubes) are used which are packed with finely grained sorbents. A solvent flows through the column during the chromatographic process, usually under a considerable pressure. Stainless steel is the most widely used material for the manufacturing of the columns, this warrants good mechanical properties of column, a sufficient resistance to pressure, and also in most cases, satisfactory resistance to corrosion, which may be caused by liquids applied as mobile phases or also by analyzed compounds. The columns are sealed with gaskets made of metal or of a suitable plastic material. The design of sealing fittings has to warrant minimum dead volume at the inlet and outlet ends of the column and the absence of an undesirable spreading of the sample by the flowing liquid during the chromatographic process.

Numerous designs exist for this purpose which meet the requirements mentioned above, but which also exhibit some negative effects in the liquid chromatography following in principle from the conception and material which have been used until now.

In the first place, the application of metallic columns is limited by the corrosion resistance of the material itself (stainless steel), which is very good in most organic solvents but unsatisfactory in a long-termed contact with organic acids, halogenated hydrocarbons, and their decomposition products. The metallic columns are substantially less resistant to the action of aqueous solutions of acids and salts commonly used in the reversed-phase chromatography, ion-exchange chromatography, and affinity and gel chromatography of biopolymers. Moreover, irreversible changes of the sample may take place during the contact of metal with mixtures of sensitive biologically active compounds, which are still more often separated by liquid chromatography.

The problems with the precise machining of metallic materials are of similar importance, because most of the common column designs are relatively complex. A high-quality polish of the inner surfaces of the tubes is the essential condition for the successful packing and use of columns. These facts are manifested by the relatively high production cost of the manufacturing of metallic columns. The usual design has in most cases a single-purpose manner of use and a limited life. The whole column has to be replaced if the chromatographic regime is varied or if its efficiency decreases.

The design principle analogous to that for metallic columns was also utilized in the manufacturing of glass columns (e.g. Czechoslovak Certificate of Authorship No. 183,468). Glass columns have numerous advantages in liquid chromatography, their main advantage being their high chemical resistance to the action of aggressive mobile phases or separated compounds. The high quality of the inner surface of glass tubes is of similar importance, because it reduces to a minimum the spreading of zones caused by any unevenness of the inner surface. On the other hand, the considerable brittleness of glass, its low pressure resistance, and the necessity of the shaping of glass columns for the setting of sealing fittings make difficult the utilization of recently known constructions of glass columns in high-performance liquid chromatography. Designs using a metallic jacket for the compensation of the inner pressure in the column by the outer pressure are rather demanding and expensive.

SUMMARY OF THE INVENTION

The invention has among its objects the provision of a column for liquid chromatography which comprises a glass tube placed inside a jacket with dismantlably connected sockets, the faces of which press by their inner surfaces against seals furnished with openings for the inlet and outlet of liquid. The seal may be advantageously placed in a bushing supporting the glass tube in the jacket and inserted between the inner wall of the jacket and the outer wall of the glass tube. The bushing may be adhesive-bound to the glass column, and the seal including a gasket, carrying a permeable partition in its recess, can be inserted into openings of the bushing. The bonding between the metallic bushing and the glass tube may be also advantageously realized by means of a low-melting alloy having a melting point of 60–250 degrees C, consisting of elements selected from the group which comprises bismuth, lead, tin, cadmium, zinc and antimony.

In another embodiment in accordance with the invention, the column consists of a bushing manufactured from metal, which has radial grooves made in its inner wall, the bushing being provided with an insert made of plastic material having a step on its outer side, such insert fitting into the grooves of the bushing, while the insert has a permeable partition inserted into the bottom which bears on the face of the glass tube.

As the jacket does not come into contact with the mobile phase being analyzed, the jacket can also be made from metals of lower corrosion resistance, such as aluminum, brass, or even from a plastic material selected from the group comprising polyamides, polypropylene, polyvinyl chloride, polyester resins, phenol-formaldehyde and urea-formaldehyde resins. The sockets may be also made of this material and lined with a corrosion resistant part made, e.g., of stainless steel or glass. The walls of the jacket may be perforated to enable visual observation of the chromatographic process and the quality of the packing.

The columns according to the invention may be connected in series in a simple way without using interconnection capillaries, which increase the spreading of zones. Liquid tightness is attained by pressure exerted by the sockets upon the seals of the glass tube.

The columns according to the invention also remove the above-mentioned shortcomings of recent constructions of glass columns. During operation, the relatively brittle glass tube is placed in the strong protective jacket, a low pressure resistance of the glass can be enhanced by chemical reinforcement, e.g. by a process described in the Czechoslovak authorship certificate No. 183,468, and the ends of the glass tube need not be broadened, because the axial pressures arising during column operation are transferred by the bushings on the metallic jacket and the seals of the glass column are not stressed.

The glass tube may be advantageously reinforced by a surface layer of potassium ions attained by their diffusion into glass at elevated temperature. This finish enhances the resistance of the glass tube towards the action of pressure during packing with a sorbent, and also during high-performance liquid chromatography.

In addition to the high chemical resistance of glass and the perfect inner surface of the tube, a considerable advantage is also the possibility of observing visually the chromatographic separation and the quality of packing through one or several sight holes in the jacket. The glass tubes packed with various sorbents may be replaced in the single jacket by a simple operation without tools in the various ways required for various types of chromatographic analyses. The possibility of replacing the tubes brings a substantial reduction of costs for the set of columns packed with various sorbents. To replace the original column by a new one, only the inner glass tube packed with the needed sorbent needs to be provided. The connection of columns in series enables the easy formation of various combinations on the principle of a building-block system, including the incorporation of short protection precolumns.

The columns according to the invention represent an economically advantageous solution not only for the user but also for the producer. Because a number of machining operations are omitted in the manufacturing of each single column, the extent of work and the cost of metallic material are reduced. The design of columns according to the invention allows a substantial increase in the proportion of mechanized and automated operations in their manufacturing and packing with sorbents.

BRIEF DESCRIPTION OF THE DRAWING

With these and other objects in view, which will become apparent in the following detailed description, the present invention, which is shown by example only, will be clearly understood in connection with the accompanying drawing, in which.

DESCRIPTION OF THE PREFERRED EMBODIMENTS

Figure 1:
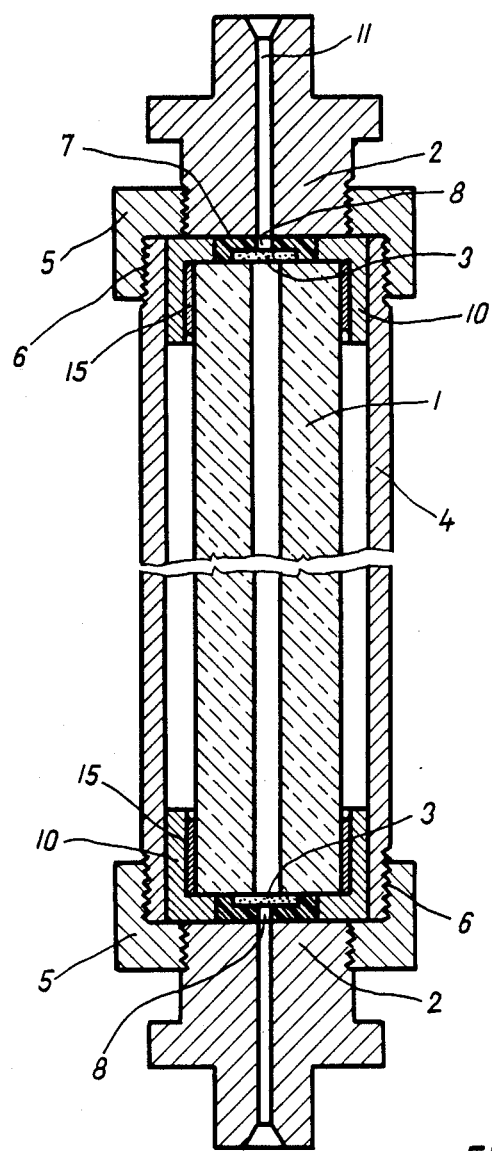
FIG. 1 shows a first embodiment of assembled column with the jacket according to the invention.

The column in FIG. 1 consists of the glass tube 1 for a sorbent packing which is placed in a metal jacket 4 with threads 6 on its outer ends. The glass tube 1 is provided with a seal at each end. Each seal consists of a permeable partition 3, and a bushing 7 placed axially outwardly of each partition and provided with a central opening 8. Each bushing 7 is inserted into a respective cap-shaped bushing 10. Each bushing 10 is bound by a sleeve-shaped cementing insert 15 to the outer end of the glass tube 1, thus centering the glass tube 1 with respect to the jacket 4. In its lengthwise, axial direction, the glass tube is fixed with respect to the jacket 4 by means of sleeve nuts 5. A centrally bored plug 2, against which the bushing 7 bears, is screwed into the respective member 5.

The central channel 11 in each member 2 is coaxial with the opening 8 in the associated bushing 7. The members 5 have an internal thread 6 for connection with the external threads on jacket 4. The column jacket 4 can be made of brass, stainless steel or plastic material, e.g. from polyvinyl chloride, polypropylene, polyester or polyamide. Sight holes (not shown) for visual observation of a chromatographic process can be provided in the wall of the jacket. The bushing 7 is made from a plastic material, preferably from polytetrafluoroethylene. The permeable partition 3 is made as a porous plate of multi-perforated stainless steel, polytetrafluoroethylene or glass, or as a metallic net. The bushings 10 have an outer diameter such to pass slidingly through the jacket 4. After screwing the sockets 5 into the jackets 4, the axially inner end of member 5 fits on the bushing 7 and the column is ready for use.

The cementing insert 15 may be made also in such a way that the space between the outer surface of the glass tube 1 and the inner surface of the bushing 10 is filled with a fused low-melting metallic alloy heated by 0.5 to 150 degrees C. above its melting point. For example, alloys of bismuth, lead, tin, cadmium, zinc and antimony with melting points ranging between 60 and 250 degrees C. may be advantageously used. The alloy contracts during solidification, as the metallic fitting does also on cooling, and adheres very firmly to the glass tube. The radial prestress of glass possible formed acts in this case favorably against radial pressures acting in the opposite direction during the chromatographic process and reinforces the most stressed end of the column.

For fitting the bushing 10 on the glass tube 1, a centering pin (not shown) made of polytetrafluoroethylene may be advantageously used, in order to secure the correct geometry of the column end, fixes the relative positions of the glass tube 1 and the bushing 10 as long as the low-melting alloy is liquid, and thus simplifies the whole operation.

Figure 2:
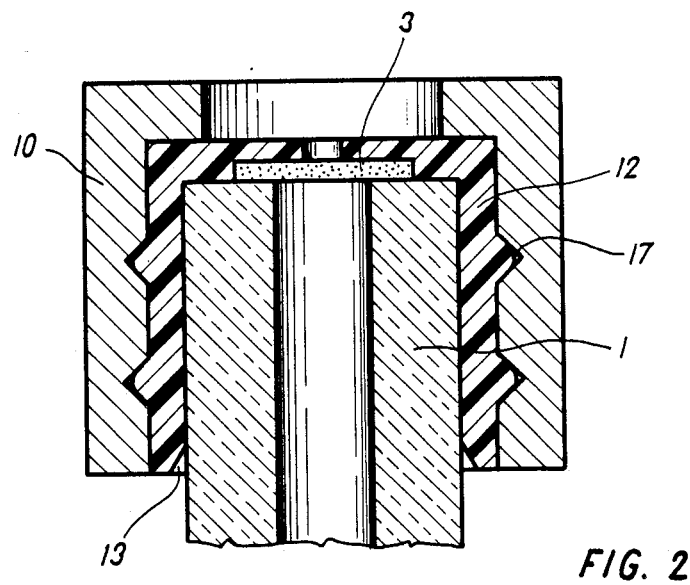
FIG. 2 illustrates an alternative construction of the column seal.

As shown in FIG. 2, the seal of the glass tube 1 may also be placed in a cylindrical bushing 10 made of metal which has the shaped inner walls with grooves 17. The bushing 10 is filled with an insert 12 of plastic material, e.g. polytetrafluoroethylene, having an internal bevel on taper 13. The inner diameter of the cylindrical part of the insert 12 is smaller than the outer diameter of the glass tube 1 and the porous partition 3 is placed inside the insert 12. After pressing the glass tube 1 in the bushing 10, the plastic material fills the recess in the bushing 10 and the tube is fixed by the thus produced tension.

Figure 3:
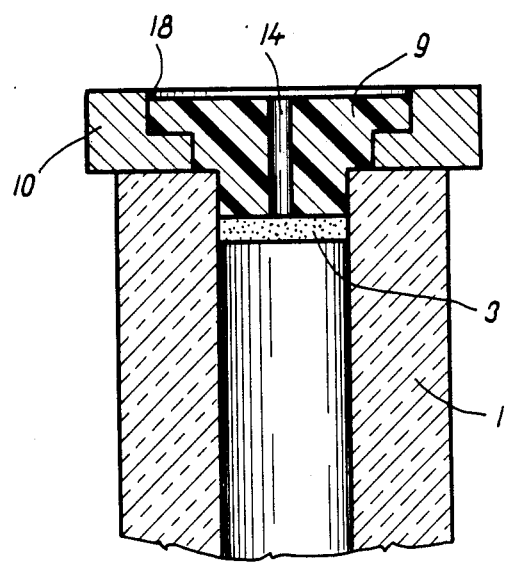
FIG. 3 shows a second alternative design of the column seal.

Another type of seal of the tube 1 is shown in FIG. 3. It is formed by a plug 9 made of plastic material with a drilled axial hole 14, which plug fixes the porous partition 3 and at its broadened end fits into the step 18 of a bushing 10'. The mechanism of sliding the glass tube 1 with seals into the jacket 4 and of its tightening is the same as in FIG. 2, wherein the bushing 10 is adhesion-bound to the glass tube 1.

Figure 4:
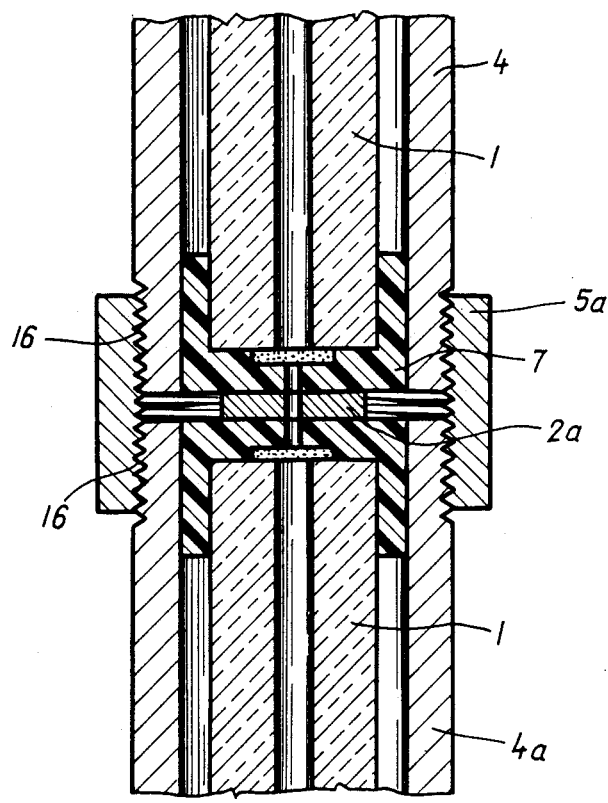
FIG. 4 shows a further design of seal and socket adapted for the connection of the columns in series.

Individual columns furnished with jackets may be connected in series, as shown in FIG. 4. A face member 2a bears on both sides against the bushings 7 of seals of both the connected columns. The connection between the columns is secured by a sleeve member in the form of a doubled socket 5a furnished at both sides with threads 16 for screwing on the respective jacket 4, 4a.

In case the temperature of the glass tube 1 is controlled by means of a thermo-regulating medium, the glass tube 1 can be sealed to the jacket 4 and furnished with inlet and outlet openings for the attachment of the piping of the thermo-regulating medium. The seal can be accomplished e.g. by O-rings disposed in annular grooves provided in the outer wall of the bushings 10.

Moreover, the jacket 4 can be provided with one or several glass-covered or free sight holes (not shown) serving for the visual observation of the column packing.

For the sake of a detailed illustration, one actual construction of the chromatographic column according to the invention follows.

The column is constructed according to FIG. 1. The glass tube 1 is made of borosilicate "SIAL" (trademark) glass having an inner diameter of 3 mm and a wall thickness of 2.5 mm. The glass tube is 100 mm long. The seals 2, made according to FIG. 1, are adhesive-bound to the tube 1 and the porous partitions 3 are in the form of nets of stainless steel of a mesh diameter of 3 um and fixed with a polytetrafluoroethylene gasket 7. The outer jacket 4 is made of a brass tube with an inner diameter of 12 mm and a wall thickness of 2.5 mm, with two sight holes milled out lengthwise opposite one another. The ends of jacket 4 are furnished with threads 16, on which the brass members 5 are screwed with stainless steel members 2, provided with the opening and outer thread for fitting of connection capillaries. The column is packed with microparticulate spherical silica gel of a grain size of 5 um at a pressure of 40 MPa and attains the efficiency of 25,000 theoretical plates per meter of column length. The pressure testing of an empty column revealed that the glass tube 1 treated by the surface diffusion of potassium ions resists an internal pressure of 80 MPa without destruction.

The bushing 10 is fastened to the glass tube 1 in the following way: The stainless steel bushing has an outer diameter of 10 mm, an inner diameter of 9 mm, and a length of 8 mm, having the inner recess 18 with a diameter of 6.5 mm and a height of 2 mm, was first placed on a polytetrafluoroethylene centering pin, which was stepwise machined to the diameters 3.5 and 6.5 mm. About 0.7 g of an alloy consisting of 50% bismuth, 25% lead, 14.5% tin and 12.5% cadmium (melting point 60.6 degrees C.) was inserted into the recess of the bushing. This assembly was, together with the end of a glass tube 1 having an inner diameter of 3.5 mm and an outer diameter of 8.3 mm, heated to 90 degrees C. by a stream of warm air and then the glass tube 1 was immediately slid into the stainless steel bushing 10 and centered by means of the pin.

The excess of the displaced alloy was removed still in liquid state and, after solidification, thoroughly cut by a knife and the centering pin was pulled out. The stainless steel bushing 10 cannot be then removed from the glass tube 1 even by means of pliers. The composition of the alloy depends on the chosen melting point and may be found, for example, in the book by V. J. Perelman: "Small Chemical Handbook" (Czech translation from Russian, 1954), p. 473, wherein there are disclosed alloy compositions corresponding to the melting point range of 60 to 250 degrees C. Such compositions include some or all of the following individual elements: bismuth—up to 70%; lead—up to 90%; tin—up to 100%; cadmium—up to 50%; zinc—up to 15%; and antimony—up to 15%.

Although the invention is illustrated and described with reference to a plurality of embodiments thereof, it is to be expressly understood that it is in no way limited to the disclosure of such preferred embodiments but is capable of numerous modifications within the scope of the appended claims.

We claim:

1. A column for liquid chromatography comprising
   a glass tube for sorbent packing,
   a jacket surrounding the glass tube provided with connecting means on both ends, said jacket and glass tube forming an interspace so that said jacket does not come in contact with a mobile phase being analyzed thereby allowing the jacket to be made from metals of lower corrosion resistance,
   a first bushing having an opening and positioned on the end of the glass tube and adapted to space apart the glass tube and the jacket,
   said first bushing being adhesive bound to an outer portion of the end of the glass tube,
   a second bushing comprising a seal located in the opening of the first bushing, said seal being a gasket and a permeable partition, and
   removable sockets connected to each of said connecting means, each of said sockets including an element having a surface adapted to abut a respective seal, each of said sockets being adapted to cooperate with a respective connection means such that said element can exert a comprehensive pressure on a respective seal, and
   each of said sockets including an opening for conduction of liquid, said opening communicating with the interior of the glass tube.

2. The column according to claim 1, wherein the glass tube has been reinforced by the surface diffusion of suitable ions.

3. The column according to claim 1, wherein the bushing is made of metal, has radial grooves in its inner wall, and is furnished inside with an insert made of plastic material, the insert having a bottom bearing on the face of the glass tube and containing the inserted permeable partition.

4. The column according to claim 1, wherein the bushing rests on the face of the glass tube and has a step around its opening, and a plug with the inserted permeable partition disposed in the step.

5. The column according to claim 1, wherein the jacket is made of metal selected from the group comprising stainless steel, aluminum and its alloys, brass and titanium, or of plastic material selected from the group comprising polyamides, polypropylene, polyvinyl chloride, polyester resins, phenol-formaldehyde resins and urea-formaldehyde resins.

6. The column according to claim 1, wherein a face member is separated from the socket, the socket being doubled-ended and furnished at both ends with threads adapted for connection with the jacket of another column.

7. The column according to claim 1, wherein the jacket is provided with openings for the inlet and outlet of thermo-regulating liquid medium.

8. The column according to claim 1, wherein the column jacket is furnished with one or several sight holes for visual observation of the column packing.

9. The column according to claim 1, wherein the bushing is fixed to the glass tube by means of a low-melting alloy having a melting point of 60 to 250 degrees C., which alloy consists of elements selected from the group comprising bismuth, lead, tin, cadmium, zinc and antimony.

* * * * *

UNITED STATES PATENT AND TRADEMARK OFFICE
CERTIFICATE OF CORRECTION

PATENT NO. : 4,968,421

DATED : November 6, 1990

INVENTOR(S) : Pavel Spacek et al

It is certified that error appears in the above-identified patent and that said Letters Patent is hereby corrected as shown below:

Cover page, column 1, item 30, delete line 3 in its entirety, and substitute therefor —July 23, 1981 Czechoslovakia 5650-81—.

Signed and Sealed this

Twelfth Day of February, 1991

Attest:

HARRY F. MANBECK, JR.

*Attesting Officer*   *Commissioner of Patents and Trademarks*